United States Patent [19]

Eiffler et al.

[11] Patent Number: 5,476,888
[45] Date of Patent: Dec. 19, 1995

[54] DIPHOSPHINES

[75] Inventors: Jürgen Eiffler, Stade; Günter A. Jüptner, Hammah, both of Germany; David P. Flores, Lake Jackson, Tex.

[73] Assignee: The Dow Chemical Company, Midland, Mich.

[21] Appl. No.: 300,682

[22] Filed: Sep. 2, 1994

[51] Int. Cl.$^6$ .......................... C07F 9/50; C08K 5/5333; C08K 5/521; C08K 5/50
[52] U.S. Cl. .......................... 524/123; 524/125; 524/127; 524/154; 558/160; 558/162; 558/165; 558/274; 556/404; 560/86
[58] Field of Search .................. 524/154, 123, 524/125, 127; 568/13; 556/404; 558/274, 22, 45, 160, 162, 165; 560/86

[56] References Cited

U.S. PATENT DOCUMENTS

| | | | |
|---|---|---|---|
| 3,257,460 | 6/1966 | Gordon et al. | 568/13 |
| 3,644,530 | 2/1972 | Bloom et al. | 568/13 |
| 4,083,803 | 4/1978 | Oswald et al. | 556/404 |
| 4,092,288 | 5/1978 | Calkins et al. | 260/37 |
| 4,145,525 | 3/1979 | Dixon et al. | 528/404 |
| 4,444,978 | 4/1984 | Dick et al. | 528/167 |
| 4,474,937 | 10/1984 | Bales | 528/169 |
| 4,627,949 | 12/1986 | Dhein et al. | 264/101 |
| 4,835,202 | 5/1989 | Pastor et al. | 524/154 |
| 4,962,144 | 10/1990 | Babillis et al. | 524/118 |
| 5,128,437 | 7/1992 | Westeppe et al. | 528/201 |

FOREIGN PATENT DOCUMENTS

| | | |
|---|---|---|
| 0423562 | 4/1991 | European Pat. Off. . |
| 960960 | 9/1982 | U.S.S.R. . |

Primary Examiner—Veronica P. Hoke

[57] ABSTRACT

The diposphines have the formula (I)

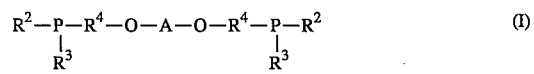

wherein:

$R^2$, $R^3$ and $R^4$ independently from each other represent a hydrocarbyl group which is substituted with one or more radicals selected from the group consisting of halogen, alkyl and alkoxy, and A is —C(O)—, —S(O)$_2$—, —S(O)— or certain divalent organic groups.

The diphosphines are useful for stabilizing thermoplastic polymers, such as polycarbonates, against thermal discoloration.

16 Claims, No Drawings

DIPHOSPHINES

BACKGROUND OF THE INVENTION

The present invention relates to a diphosphine, a process for preparing it and to the use of the diphosphine for stabilizing a thermoplastic polymer against thermal discoloration. Furthermore, the present invention relates to a polymer composition containing a thermoplastic polymer and the diphosphine.

It is generally known in the art that most of the known thermoplastic polymers are affected to a certain extent when they are exposed to heat. The deterioration of the polymers often results in yellowing of the polymer and in degradation of its molar mass. Therefore, it is common to treat thermoplastic polymers with stabilizers. A large variety of stabilizers have been suggested in the prior art for the various thermoplastic polymers.

It has been suggested to utilize certain organic phosphites, phosphonites or phosphines, optionally in combination with epoxides or polydialkylsiloxanes, for stabilizing polycarbonates against thermal or thermal-oxidative degradation.

For example, U.S. Pat. No. 4,092,288 discloses color stable polycarbonate compositions consisting of an aromatic polycarbonate resin having in admixture therewith 0.005 to 0.5 weight percent of a triaryl, trialkyl, tri(alkylaryl) or alkyl-aryl phosphine, preferably triphenylphosphine.

U.S. Pat. No. 4,627,949 discloses a process for preparing shaped articles from polycarbonates stabilized with phosphanes by a devolatilizing injection-moulding or extrusion process. The phosphanes have the formula $(R)_2PR^1$ wherein R is an unsubstituted or substituted $C_6$–$C_{14}$-aryl radical and $R^1$=R or an unsubstituted or substituted $C_1$–$C_{18}$-alkyl radical.

U.S. Pat. No. 4,835,202 discloses the use of (hydroxyphenyl)phosphine derivatives for stabilizing a wide variety of polymers against oxidative, thermal and actinic degradation.

Unfortunately, the suggested stabilizers are volatile at the high temperatures which are applied for extruding polycarbonates.

U.S. Pat. No. 4,145,525 discloses polyalkylene carbonates of improved thermal stability. At least a portion of the free hydroxyl groups is reacted with a hydroxyl reactive phosphorus compound whereby the active hydrogen on the hydroxyl group is replaced by an oxygen-phosphorus bond. Unfortunately, the oxygen-phosphorus bond can be easily hydrolyzed by acids. Accordingly, the end-capped groups are relatively instable in the presence of acids. However, traces of acids are often present when polycarbonates are washed and later extruded.

U.S. Pat. No. 4,474,937 discloses phosphorus-modified polyester carbonate resins. The repeating unit within the polymer can be a phosphonite, phosphite, phosphonate or phosphate species. The amount of phosphorus present in the polymer is 1–1000 ppm, preferably 1–100 ppm, based on the weight of the polymer. The resins exhibit improved thermal-oxidative stability compared to non-modified polyester carbonates.

U.S. Pat. No. 4,444,978 discloses the preparation of carbonate polymers having increased thermal stability by incorporating into the polymer chain an oligomer which has the formula:

R is the divalent residue of a dihydric mononuclear or a dihydric polynuclear phenol, R1 is an alkyl, aralkyl or alkaryl group having 1 to 25 carbons, and n is a number having an average value of 1 to 200. From 10 to 2000 ppm, preferably from 100 to 1000 ppm of the oligomer are copolymerized with the copolymer.

Although a wide variety of stabilizers exist for the various types of thermoplastic polymers, it is still desirable to provide new stabilizers in order to meet the ever increasing quality requirements for thermoplastic polymers.

One object of the present invention is to provide new compounds which can be used for stabilizing thermoplastic polymers, such as polycarbonates, against thermal discoloration. It is a preferred object of the present invention to provide a new stabilizer for thermoplastic polymers which is less volatile at high temperatures than the phosphines and phosphanes disclosed in U.S. Pat. Nos. 4,092,288 and 4,627,949.

SUMMARY OF THE INVENTION

One aspect of the present invention is a diphosphine of the general Formula I:

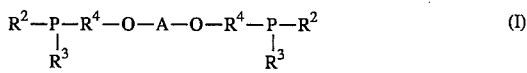

wherein:

$R^2$ and $R^3$ independently from each other represent an alkyl, cycloalkyl, aryl or aryl-alkyl group or an aryl group which is substituted at the aromatic ring with one or more radicals selected from the group consisting of halogen, alkyl and alkoxy, $R^4$ represents an alkylene, cycloalkylene, arylene or aryl-alkylene group or an arylene group which is substituted at the aromatic ring with one or more radicals selected from the group consisting of halogen, alkyl and alkoxy, and A is —C(O)—, —S(O)— or a divalent group comprising —C(O)—, —S(O)—, —P(O)— or —Si—.

Another aspect of the present invention is a process for preparing the diphosphine of Formula I wherein a compound of Formula II

wherein $R^2$, $R^3$, $R^4$ have the meanings indicated above, is reacted with a compound of formula:

wherein A has the meaning indicated above and each X independently is halogen, hydroxy or alkoxy or both X's together are an anhydride group.

Yet another aspect of the present invention is the use of the diphosphine of Formula I for stabilizing a thermoplastic polymer, such as a polycarbonate, against thermal discoloration.

Yet another aspect of the present invention is a method of stabilizing a thermoplastic polymer against thermal discoloration, which method comprises contacting the thermoplastic polymer with an effective amount of a diphosphine of Formula I.

Yet another aspect of the present invention is a polymer composition which comprises a thermoplastic polymer, such as a polycarbonate, and a diphosphine of Formula I. The polymer composition may be in various forms, for example in the form of granules or pellets or in the form of a molded article.

DETAILED DESCRIPTION OF THE INVENTION

In the diphosphine of the general Formula I

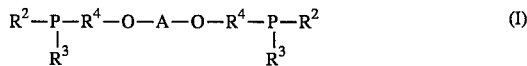

$R^2$ and $R^3$ independently from each other represent an alkyl, cycloalkyl, aryl or aryl-alkyl group or an aryl group which is substituted at the aromatic ring with one or more radicals selected from the group consisting of halogen, alkyl and alkoxy, $R^4$ represents an alkylene, cycloalkylene, arylene or aryl-alkylene group or an arylene group which is substituted at the aromatic ring with one or more radicals selected from the group consisting of halogen, alkyl and alkoxy, and A is —C(O)—, —S(O)$_2$—, —S(O)— or a divalent group comprising

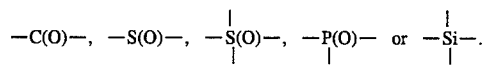

The radicals $R^2$ and $R^3$ can be identical or different.

Of the alkyl and alkylene groups those are preferred that have 1 to 18, preferably 1 to 12 carbon atoms. The alkyl and alkylene groups can be straight-chain or branched. The most preferred alkyl groups are methyl, ethyl, n-propyl, i-propyl, n-butyl, sec. butyl or tert. butyl or the pentyl, hexyl, octyl, nonyl, decyl or octadecyl groups. The most preferred alkylene groups are methylene, ethylene, n-propylene, i-propylene, n-butylene, sec. butylene or tert. butylene or the pentylene, hexylene, octylene, nonylene, decylene or octadecylene groups.

Of the cycloalkyl and cycloalkylene groups those having 5 or 6 carbon atoms are preferred, such as cyclopentyl or cyclohexyl, cyclopentylene or cyclohexylene.

Of the aryl and arylene groups those having from 6 to 14 carbon atoms are preferred, such as phenyl or naphthyl, phenylene or naphthylene. The aryl and/or arylene groups may be substituted with one or more of the above-mentioned alkyl groups and/or with one or more halogens, such as fluoro, chloro or bromo, and/or one or more alkoxy groups. Alkoxy groups, if present, preferably contain 1 to 6 carbon atoms, such as the methoxy, ethoxy, n-propoxy, i-propoxy, n-butoxy, sec. butoxy or tert. butoxy groups. If substituted, the aryl and/or arylene groups preferably are substituted with 1, 2, or 3 substituent groups.

In the aryl-alkyl groups the above-mentioned alkyl groups are preferred and the aryl group preferably is phenyl. Preferred aryl-alkyl groups are benzyl, phenyl butyl, tolyl or xylyl.

In the aryl-alkylene groups the above-mentioned alkylene groups are preferred and the aryl group preferably is phenyl. Preferred aryl-alkylene groups are benzylene, phenyl butylene, tolylene or xylylene.

If $R^4$ is cyclohexyl, phosphorus and oxygen are preferably bound in the 1,4-position to the cyclohexyl group. If $R^4$ is an optionally substituted phenylene group, phosphorus and oxygen are preferably arranged in the para-position to the phenylene group.

Preferably, $R^2$ and $R^3$ are aryl groups, most preferably phenyl, and $R^4$ is an arylene group, most preferably phenylene. The aryl and/or arylene groups preferably have from 6 to 14 carbon atoms. They are preferably unsubstituted or substituted at the aromatic ring with one or more halogens, such as bromo or chloro, one or more alkyl groups, such as the above-mentioned $C_{1-6}$-alkyl groups, and/or one or more alkoxy groups, such as methoxy, ethoxy, propoxy and/or butoxy groups.

Preferably, A is —C(O)—, —S(O)$_2$—, —S(O)— or a divalent group comprising

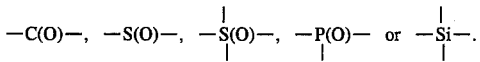

Preferred A groups are —C(O)—, —S(O)—, —S(O$_2$)—, —C(O)-alkylene-C(O)— or —C(O)-arylene-C(O)—, wherein the arylene group is optionally substituted at the aromatic ring with one or more radicals selected from the group consisting of halogen, alkyl, cycloalkyl, aryl, oxyalkyl, hydroxy, alkoxy and —C(O)—[O—$R^4$—P($R^2$)($R^3$)] and the alkylene group is optionally substituted with one or more radicals selected from the group consisting of halogen, alkyl, cycloalkyl, aryl, oxyalkyl, hydroxy, alkoxy and —C(O)—[O—$R^4$—P($R^2$)($R^3$)].

If A comprises an alkylene group, it is preferably unsubstituted or substituted with one or more alkyl and/or alkoxy groups. Preferred alkoxy groups are listed above. The most preferred alkyl groups are methyl, ethyl, n-propyl or, most preferably, isopropyl. These alkyl groups provide branching to the alkylene group. The alkylene group preferably comprises from 1 to 50, more preferably from 3 to 30, most preferably from 4 to 25 carbon atoms. Most preferably, it is linear and unsubstituted.

If A comprises an arylene group, it is preferably a phenylene group which is optionally substituted at the aromatic ring with one or more halogens, alkyl, cycloalkyl and/or alkoxy groups. Preferred halogens and alkyl, cycloalkyl and alkoxy groups are described above. The most preferred arylene group is phenylene which is preferably unsubstituted or substituted with one or more of the above-mentioned $C_{1-6}$-alkyl groups, $C_{5-6}$-cycloalkyl groups, bromo, chloro, methoxy, ethoxy, propoxy and/or butoxy groups. If A comprises an optionally substituted phenylene group, it is preferably the 1,4-phenylene group.

Alternatively, A is the group

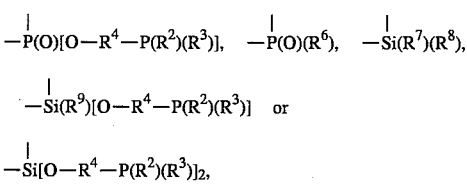

wherein $R^6$, $R^7$, $R^8$ and $R^9$ independently from each other represent an alkyl, cycloalkyl, aryl or aryl-alkyl group or an aryl group which is substituted at the aromatic ring with one or more halogens, alkyl, cycloalkyl, aryl, oxyalkyl, hydroxy or alkoxy groups. Preferred alkyl, cycloalkyl, optionally substituted aryl and aryl-alkyl groups are the same as those listed above for $R^1$ and $R^2$.

Particularly preferred diphosphines of Formula I are those wherein $R^2$ and $R^3$ are phenyl, $R^4$ is phenylene and A is —C(O)-phenylene-C(O)— or —C(O)— alkylene-C(O)—, wherein the alkylene group comprises from 3 to 20 carbon atoms.

It has been found that the diphosphines of the present invention are considerably less volatile at elevated temperatures than corresponding known phosphines which only comprise one group $(R^2)(R^3)P$—. Particularly, the diphosphines of the present invention are less volatile at temperatures which are usually maintained during processing of polycarbonates, i.e. at temperatures of more than about 200° C. Due to their lower volatility, less powerful equipment, such as ventilation, is required to keep the concentration of these compounds in air below a certain level. Furthermore, it has been found that several diphosphines of the present invention are as effective as the corresponding known monophosphines for stabilizing thermoplastic polymers, such as polycarbonates, against thermal discoloration. Surprisingly, it has been found that some of the diphosphines of the present invention are even more effective stabilizers than the corresponding monophosphines.

By the term "diphosphines" is meant that the compounds of the present invention comprises at least two groups $(R^2)(R^3)P$—$R^4$—. Depending on the meaning for A in Formula I above, the compounds of Formula I may even comprise three or more of these groups.

Another aspect of the present invention is a process for preparing a diphosphine of Formula I wherein a compound of Formula II $$R^2-P-R^4-OH \quad\quad (II)$$
$$\underset{R^3}{|}$$

is reacted with a compound of Formula III $$X-A-X \quad\quad (III)$$

wherein $R^2$, $R^3$, $R^4$ and A have the meanings indicated above and each X independently is halogen, hydroxy or alkoxy or both X's together are an anhydride group.

If $R^4$ in Formula II is an optionally substituted phenylene ring, the hydroxy group in formula II may be arranged in ortho-, meta- or para-position to the phosphorus, however it is preferably arranged in para-position to the phosphorus.

Compounds of Formula II and methods of preparing them are known in the art, for example from U.S. Pat. No. 4,835,202 and from the references cited therein.

Preferred meanings for X in Formula III are bromine, alkoxy and, more preferably, chlorine. If X is an alkoxy group, it preferably contains 1 to 6 carbon atoms, such as the methoxy, ethoxy, n-propoxy, i-propoxy, n-butoxy, sec. butoxy or tert. butoxy group.

Preferred compounds of Formula III are phosgene, $SO_2Cl_2$, dichlorodialkylsilanes and aromatic or aliphatic diacid chlorides. The most preferred compounds of Formula III are phosgene, terephthalic acid dichloride, dichlorodimethylsilane and saturated, unsubstituted aliphatic diacid chlorides comprising from 1 to 30, preferably from 1 to 20, more preferably from 3 to 20 carbon atoms in the alkylene group.

The molar ratio between the compound of formula II and the compound of Formula III generally is at least 1.7:1, preferably from 1.9:1 to 2.2:1, more preferably from 2:1 to 2.1:1, most preferably about 2:1.

Depending on the specific starting materials which are used in the reaction, an acid may be produced as a by-product. For example, HCl is produced when X in Formula III is chlorine. In such a case, preferably a base is added to the reaction mixture for neutralizing the acid. Preferably, the molar number of basic groups is at least 1, more preferably from 1.5 to 2 per mole of chlorine radical in the compound of Formula III. The preferred types of base mainly depend on the type of diluent that is used for the reaction.

The reaction temperature preferably is from 20° to 100° C., more preferably from 20° to 70° C., most preferably from 25° to 50° C., depending on the reaction diluent. The reaction is preferably conducted at about ambient pressure.

Depending on the type of reaction diluent, the reaction can be conducted a) as a two-phase process or b) in a homogeneous solution.

For conducting a two-phase process, the reaction diluent comprises an aqueous and an organic phase. The volume ratio between the aqueous phase and the organic phase preferably is from 1:2 to 2:1, more preferably from 1:1.5 to 1.5:1, most preferably about 1:1. The interphase surface area preferably is from 0.1 $m^2/l$ to 50 $m^2/l$. The reaction diluents are preferably water and one or more water-immiscible solvents, preferably one or more chlorinated solvents. Preferred chlorinated solvents are chlorobenzene, dichlorobenzene, ethylene chloride or, most preferably, methylene chloride. The most useful bases are alkali hydroxides or alkaline earth hydroxides, such as NaOH, KOH, CsOH, $Ca(OH)_2$, $Mg(OH)_2$ or the corresponding oxides which form hydroxides in contact with water, such as CaO. The two-phase process is particularly suitable if phosgene is used in the reaction.

For conducting the reaction in a homogeneous solution, generally one or more organic solvents are used which are inert towards the reactants and which are preferably polar. Preferred organic solvents are chlorinated solvents, such as chlorobenzene, dichlorobenzene, ethylene chloride or, most preferably, methylene chloride; ethers, such as dimethyl ether, tetrahydrofuran, dimethoxyethane or, most preferably, dioxane; formamides, such as dimethylformamide or dimethylacetamide; esters, such as acetic ester; or ketones, such as acetone. Most preferably, chlorinated solvents and/or ethers are used. Preferred bases are amines, more preferably tertiary aliphatic amines, such as trimethylamine or triethylamine, or aromatic amines, such as pyridine.

The above described process is particularly suitable if A is —C(O)—, —S(O)—, —S(O$_2$)—, —C(O)-alkylene-C(O)—, —C(O)-arylene-C(O)—, $$-\underset{|}{P}(O)(R^6) \quad \text{or} \quad -\underset{|}{Si}(R^7)(R^8),$$

the alkylene and arylene group optionally being substituted as described above.

If A is the group $$-\underset{|}{P}(O)[O-R^4-P(R^2)(R^3)],$$

$$-\underset{|}{Si}(R^9)[O-R^4-P(R^2)(R^3)] \quad \text{or}$$

$$-\underset{|}{Si}[O-R^4-P(R^2)(R^3)]_2,$$

the compounds of Formula I can be produced by the above-described process, however they are preferably produced as herein described.

A compound wherein A is

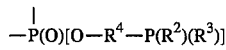

is preferably produced by reacting a compound of Formula II and P(O)X$_3$, preferably POCl$_3$, in a molar ratio of more than 2.5:1, more preferably at least 3.:1, most preferably from 3.0:1 to 3.1:1.

A compound wherein A is

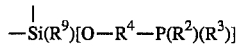

is preferably produced by reacting a compound of Formula II and Si(R$^9$)X$_3$, preferably Si(R$^9$)Cl$_3$, in a molar ratio of more than 2.5:1, more preferably at least 3:1, most preferably from 3.0:1 to 3.1:1.

A compound wherein A is

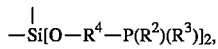

is preferably produced by reacting a compound of Formula II and SIX$_4$, preferably SiCl$_4$, in a molar ratio of more than 3.5:1, more preferably at least 4:1, most preferably from 4.0:1 to 4.1:1.

Depending on the type of reaction diluent, the reaction can be conducted a) as a two phase process or b) in a homogeneous solution, as described above for process i ).

Useful reaction temperatures, pressure, bases and reaction diluents are those described with respect to process i) above.

The diphosphines of Formula I of the present invention are very effective for stabilizing thermoplastic polymers against discoloration. Accordingly, another aspect of the present invention is a polymer composition which contains one or more thermoplastic polymers and one or more of the above described diphosphines of Formula I. The polymer composition of the present invention preferably comprises from 0.001 to 2.5 weight percent, more preferably from 0.01 to 0.5 weight percent, most preferably from 0.02 to 0.2 weight percent of one or more of the diphosphines of Formula I, based on the weight of the thermoplastic polymer. If the polymer composition of the present invention comprises more than one diphosphine of Formula I, their total weight preferably is within the indicated range.

The thermoplastic polymer preferably is a polyolefin, such as an ethylene-homo- or -copolymer or a polypropylene, a polyacrylate, polymethacrylate or poly (methyl/ methacrylate) or a styrene-homo- or -copolymer, such as polystyrene, a styrene/acrylate copolymer, copolymer of styrene, butadiene and an acrylonitrile, (an ABS polymer), a polycarbonate or a blend of such polymers. The stabilizer composition of the present invention is particularly useful for stabilizing a polycarbonate which is optionally blended with an ABS (acrylonitrile/butadiene/styrene) polymer, a polyester, such as polyalkyleneterephthalate, preferably polyethyleneterephthalate, a polystyrene, a polyarylene-sulphone or with a polyolefin. Preferred polyolefins are polyethylene or ethylene copolymers, such as ethylene/propylene copolymers, ethylene/acrylate copolymers, polypropylene, polybutene, polyisobutene or polymethylpentene. These polymers are well known in the art.

For the sake of convenience in the following paragraphs mainly polymer compositions are described which contain a polycarbonate as a thermoplastic polymer, although the present invention is not limited thereto. Suitable polycarbonates are described in U.S. Pat. No. 4,722,955, Column 2, lines 6–42 and the references cited therein. The thermoplastic polycarbonates present in the polymer compositions of the present invention generally are polycondensates which are obtainable by reacting a diphenol with a carbonate precursor, such as phosgene, a haloformate, an acid chloride, preferably a difunctional acid chloride, such as terephthalic acid chloride, or a carbonate ester. Aromatic polycarbonates are preferred.

Preferred diphenols are those of formula HO—ZO—H, wherein Z comprises a mononuclear or polynuclear aromatic group of 6 to 30 carbon atoms, to which the hydroxy groups are directly linked. The aromatic group may comprise a heteroatom and may be substituted with one or more groups, for example, one or more halogens and/or one or more alkyl or cycloalkyl groups. Preferred diphenols are hydroquinone, resorcinol, dihydroxybiphenylenes, bis( hydroxyphenyl)alkanes, bis(hydroxyphenyl)cycloalkanes, bis(hydroxyphenyl)fluorenes, bis(hydroxyphenyl)ethers, bis(hydroxyphenyl)sulfides, bis(hydroxyphenyl)ketones, bis(hydroxyphenyl)sulfones, his(hydroxyphenyl)sulfoxides and alpha,alpha'bis(hydroxyphenyl)diisopropylbenzenes and derivatives thereof which are halogenated and/or alkylated at the nucleus. Other examples of suitable diphenols which are useful as star ting materials for the polycarbonates are listed in U.S. Pat. No. 4,627,949, Column 2, line 68 to Column 3, line 22, in U.S. Pat. No. 4,962,144, Column 2, lines 17–46 and in European Patent Application EP-A-0 423 562, page 2, lines 24–55 and page 3, lines 1–19. Preferred diphenols are 2,2-bis(3,5-dibromo-4-hydroxyphenyl)propane, 4,4'-dihydroxydiphenyl, 1,1-bis( 4-hydroxyphenyl)-cyclohexane, 1,1-bis-(4-hydroxyphenyl)- 3,3,5-trimethylcyclohexane, 1-phenyl-2,2-bis(4-hydroxyphenyl)propane (phenyl substituted hisphenol A), 9,9-bis-(4-hydroxyphenyl)fluorene and, most preferably, 2,2-bis(4-hydroxyphenyl)propane (bisphenol A). Mixtures of two or more different diphenols may be used, for example, a mixture comprising 3 to 97 weight percent of bisphenol A and 97 to 3 weight percent of another bisphenol.

Most preferably, the polycarbonate is prepared from bisphenol A and phosgene. The polymer composition of the present invention preferably contains an aromatic, transparent polycarbonate.

Polycarbonates and methods of producing them are well known in the art. For example the polycarbonate can be prepared by a homogeneous organic solution process, a melt process or, preferably, a known interfacial two phase process. U.S. Pat. No. 4,092,288 discloses aromatic polycarbonates and methods of preparing them in Column 4, lines 4–68 and in Example 1. Alternatively, polycarbonates can be prepared from diphenylcarbonate or dimethylcarbonate by transesterification. These processes are described by D. Freitag et al., *Encyclopedia of Polymer Science and Engineering*, Vol. 11, pages 651–654 and the references cited therein.

Branched polycarbonates are also suitable. If the polycarbonate is branched, it preferably contains from 0.01 to 3%, more preferably from 0.05 to 2% of a branching agent, based on the weight of the polycarbonate. Branched-polycarbonates, methods of preparing them and suitable branching agents are for example described in the published European Patent Application EP-A-0 423 562, page 3, line 43 to page 4, line 2. Useful branching agents have three or more functional groups, preferably three or more phenolic hydroxyl groups. Preferred branching agents are 1,3,5-tris(4-hydroxyphenyl)benzene, 1,1,1-tris(4-hydroxyphenyl)ethane, tris(4-hydroxyphenyl)-phenylmethane, 2-4-hydroxyphenyl-2-2,4-dihydroxyphenylpropane, etc.] Other useful branching agents are trimesic or trimellitic acid or acid chlorides, 2,4-dihydroxybenzoic acid, cyanuric chloride or 3,3-bis-(4-hydroxy-3-methylphenyl) 2-oxo-2,3-dihydroindol.

Blends of a linear polycarbonate and a branched polycarbonate are also suitable.

The polycarbonates preferably have a number average molecular weight of from 10,000 to 250,000, more preferably from 12,000 to 120,000 and most preferably from 15,000 to 45,000.

The end groups of the polycarbonate may be the same or different. The most preferred end groups are p-tert-butyl phenyl, p-octyl phenyl, or phenyl. End groups which can lead to a crosslinking of polycarbonate such as arylcyclobutene-terminated carbonate polymers are particularly useful. Known chain terminators can be used, such as tert-butyl phenol, phenol or other $C_{1-7}$-alkyl phenols. Other preferred chain stoppers and their useful amounts are disclosed in European Patent application EP-A-0 423,562, page 4, lines 5–21.

The diphosphines of the present invention are particularly efficient when the polymer composition of the present invention contains an inorganic or organic light diffuser. Light diffusers are generally used for introducing light-scattering properties into transparent polymers. Polymer compositions containing light diffusers are widely used in the electrical and lightening industry, for example, as luminaries etc. Unfortunately, many of the known light diffusers are sensitive towards heat and/or oxygen. Surprisingly, it has been found that the above-described diphosphines are very efficient for stabilizing a thermoplastic polymer against thermal discoloration, even when a light diffuser has been compounded into the polymer.

If present, the polymer composition generally contains a light diffuser in an amount of from 0.1 to 10 weight percent, preferably from 0.2 to 5 weight percent, more preferably from 0.5 to 3 weight percent, based on the weight of the thermoplastic polymer, such as polycarbonate.

Preferred inorganic light diffusers are barium sulphate, titanium dioxide and blends thereof.

Organic light diffusers and methods of preparing them are known, for example, from German Offenlegungsschrift 21 46 607. Preferred organic light diffusers are known from the published European Patent Application EP-A-0,269,324. This light diffuser comprises particles of a core/shell morphology which have an average diameter of from 2 to 15 micron, a particle size distribution such that at least 90% by weight of the particles fall within ±20% of the average particle diameter, a core of rubbery alkyl acrylate polymer, the alkyl group having from 2 to 8 carbon atoms, copolymerized with 0 or up to 5% cross-linker and 0 or up to 5% graft-linker (based on the total weight of the core), and one or more polymer shells. The shells comprise from 5 to 40% of the weight of the particles. All the shells or only the outermost shell are preferably a polymer of an alkyl methacrylate, a vinyl arene, a vinyl carboxylate and/or an alkyl acrylate. Further details on the light diffuser comprising particles of a core/shell morphology and methods of preparation are disclosed in European Patent Application 0,269, 324 the teaching of which is incorporated herein by reference.

The average particle diameter of the organic light diffuser generally is from 0.1 to 100 microns, preferably from 1 to 15 microns. The particles are preferably of spherical shape.

The polymer composition of the present invention may contain optional additives, such as optical brighteners or fluorescent dyestuffs, pigments or colorants, tackifiers, mold release agents, impact modifiers, fillers, etc. Such optional additives are generally known in the art. If present, the polymer composition of the present invention contains an optical brightener or a fluorescing dye preferably in an amount of from 0.01 to 3 weight percent. The amount of pigments or colorants preferably is from 0.0001 to 5 weight percent, if present at all. Preferred mold release agents are known esters of long fatty acids; their preferred amount is from 0.01 to 2 weight percent. Preferred fillers are glass fibers, their preferred amount is from 1 to 30 weight percent. All percentages are based on the weight of the thermoplastic polymer in the polymer composition.

The polymer composition of the present invention may contain one or more other heat stabilizers, anti-oxidants, and/or UV stabilizers, such as phosphites, hypophosphites, phosphonites or, preferably, one or more hindered phenols. Hindered phenols and their use as antioxidants are described in Ullmann's *Encyclopedia of Industrial Chemistry*, Volume 3, "Antioxidants", pages 95–98, 5th ed., 1985, VCH Verlagsgesellschaft mbH and in *Encyclopedia of Polymer Science and Engineering*, Vol. 2, "Antioxidants," pages 75–91, 1985 by John Wiley & Sons, Inc. If present, the amount of such an additive generally is from 0.01 to 5%, preferably from 0.05 to 2%, more preferably from 0.1 to 1%, based on the weight of the thermoplastic polymer in the polymer composition. An additional heat stabilizer may be present, depending on the type of thermoplastic polymer. For example, if the polymer composition is substantially comprised of a polycarbonate, the presence of an additional heat stabilizer may be advantageous. If a polycarbonate is blended with a substantial amount of another thermoplastic polymer like polyolefins, vinyl-containing polymers, such as polymethyl methacrylates, the presence of an additional heat stabilizer is generally not necessary. If an additional heat stabilizer is used, its amount is generally only 0.01 to 0.5 percent, based on the weight of the thermoplastic polymer.

For preparing the polymer composition of the present invention an effective amount of the diphosphine of Formula I is mixed with the thermoplastic polymer. Effective amounts are indicated further above. One or more optional additives, such as an above-described light diffuser etc., may be mixed with the thermoplastic polymer prior to, simultaneously with or after the addition of the diphosphine of Formula I. The mixing temperature is not very critical. Room temperature is the most convenient one, however, decreased or elevated temperatures are also useful. However, it is advisable to mix the diphosphine with the thermoplastic polymer, which may contain optional additives such as a lightdiffuser etc., before the thermoplastic polymer is processed to granules or pellets. Most preferably, the diphosphine is admixed before the thermoplastic polymer is subjected to any processing or compounding step at elevated temperature. The manner of dispersing or mixing the diphosphine(s) of Formula I and any optional additives with the thermoplastic polymer(s) is not critical. However, the process chosen should be one which results in a great degree of dispersion of all the additives throughout the thermoplastic polymer. Preferred mixing equipment are mixing rolls, ribbon blenders, dough mixers, Banbury mixers, etc. The mixture can then be processed to granules or pellets by known extrusion techniques. The mixture may be fed into an extruder and extruded to a strand which is then granulated into pellets or granules. A preferred method is a devolatilizing extrusion process as generally described in U.S. Pat. No. 4,627,949. If the polymer composition contains a polycarbonate, the extrusion is preferably conducted at a temperature of from 200° to 390° C., more preferably from 230° to 380° C., most preferably from 260° to 370° C.

The pellets or granules may be formed into shaped articles in a generally known manner, for example by compression molding, injection-molding, casting techniques, etc. A preferred processing method is a devolatilizing injection-molding as generally described in U.S. Pat. No. 4,627,949. If the polymer composition contains a polycarbonate, the injection-molding is preferably conducted at a temperature of from 200° to 380° C., more preferably from 230° to 370° C., most preferably from 260° to 370° C. Examples of shaped articles are sheets, lamp covers, etc.

The invention is further illustrated by the following examples which should not be construed to limit the scope of the present invention. Unless otherwise mentioned all parts and percentages are weight parts and weight percentages.

EXAMPLES 1 TO 9 AND COMPARATIVE EXAMPLES A TO M

Several physical properties are measured as follows:

The Melt Flow Rate (MFR) is measured according to ASTM D 1238-88.

The Yellowness Index number (YI) is measured according to ASTM D 1925-70. The Yellowness Index number is an indication of discoloration of the polycarbonate composition. The lower the number, the lower is the yellowness of the polycarbonate composition due to discoloration.

The total light transmittance and light diffusion are measured according to ASTM D-1003.

The following stabilizers are used in the examples and comparative examples:
Stabilizer I: Bis(diphenyl 4,4'-hydroxyphenyl phosphine) carbonic acid ester prepared according to Example 1 below.
Stabilizer II: Bis(diphenyl 4,4'-hydroxyphenyl phosphine) terephthalic acid ester prepared according to Example 2 below.
Comparative Stabilizer III: Triphenylphosphine.
Comparative Stabilizer IV: Tetrakis-(2,4-di-tert-butylphenyl)- 4,4'-triphenylene-diphosphonite, commercially available as Sandostab PEPQ (Trademark).
Comparative Stabilizer V: 1,4-Bis(diphenylphosphino)butane, available from Aldrich.
Stabilizer VI: Bis(diphenyl 4,4'-phenoxy phosphine) dimethyl silane.
Example 1
Preparation of the Diphosphine
Bis(diphenyl 4,4'-hydroxyphenyl phosphine) carbonic acid ester, i.e., a compound of Formula I wherein $R^2$ and $R^3$ are phenyl, $R^4$ is phenylene and A is C(O), is produced according to the following procedure:

A flask is fitted with a reflux condenser, a dropping funnel, an agitator, and an inlet pipe for nitrogen and for liquid addition. The system is flushed with nitrogen. 5.6 g of diphenyl 4-hydroxyphenyl phosphine are brought into the flask and flushed with nitrogen again. 20 mL of 1.5 molar caustic are purged with nitrogen and dropped into the flask. Then 12.5 mL of a 5% solution of bis(trichloromethyl)carbonate (which forms phosgene by rearrangement) in dichloromethane are slowly added. Then 2 mL of 10% caustic are added. A second portion of 12.5 mL of the solution of bis(trichloromethyl)carbonate in dichloromethane is added, followed by the addition of 20 mL of 10% caustic. Then 0.03 g of triethylamine in 20 mL of dichloromethane are added. The reaction is performed at 25° C. After completion of the reaction, the two phases of the reaction mixture are separated by gravimetric settling. A slight nitrogen purge is maintained during the purification procedure. The aqueous phase is removed from the flask. Then 20 mL of 10% aqueous hydrochloric acid is added into the flask and the mixture is agitated. After gravimetric settling and removal of the aqueous phase, the remaining phase is washed three times with 20 mL of water. Then dichloromethane and subsequently remaining traces of water are removed under vacuum. A white powder of bis(diphenyl 4,4'-hydroxyphenyl phosphine) carbonic acid ester is obtained.

The melting point Fp of the compound is 133° C., as measured by Differential Scanning Calorimetry. The structure of the compound is confirmed by IR, $^1$H—NMR and $^{31}$P—NMR. The purity of the compound is more than 96%, the yield is 71%, based on the amount of diphenyl hydroxyphenyl phosphine.

IR-Spectroscopy: 1773 cm$^{-1}$ (C=O); 1586 cm$^{-1}$ (C—C aromate); 1492 cm$^{-1}$ (C—C aromate); 744 cm$^{-1}$ (mono-substituted aromate); 695 cm$^1$ (mono-substituted aromate).

$^{13}$—C—NMR (in CDCl$_3$): 121, 128, 132, 133, 135 ppm (aromatic), 151 ppm (C=O, ester-bond).

$^{31}$—P—NMR (in CDCl$_3$): −6.25 ppm (Singulett, phosphine) (calibrated with H$_3$PO$_3$).

The weight loss of the compound at elevated temperatures is measured by TGA (Thermal Gravimetric Analysis) at 10° C./min. under nitrogen. The weight loss is as follows:

| Temperature (°C.) | Weight loss (%) |
| --- | --- |
| 300 | 5.5 |
| 393 | 32 |
| 440 | 54 |
| 562 | 85 |

The comparison with triphenyl phosphine shows that the compound of the present invention is much less volatile than triphenyl phospine at temperatures which are usually used for extruding polycarbonates. Triphenyl phosphine volatilizes completely at TGA test conditions at 300° C.
Use of the Diphosphine as a Stabilizer Polycarbonate pellets prepared by interfacial polycondensation of bisphenol A and phosgene are used as a base resin. The polycarbonate has a melt flow rate of 3.3, a violet-blue color and a Yellowness Index of 1.4. 1000 ppm of Cetiol (trademark) as a tackifier is homogeneously distributed on the polycarbonate pellets. Then 2.25% of barium sulphate (commercially available as K3 from Sachtleben), 150 ppm of titanium dioxide, 4000 ppm of Tinuvin 234 (trademark) as a UV stabilizer, 1300 ppm of Uvitex (trademark) as an optical brightener and a heat stabilizer of the type and concentration listed in Table 1 below are added. The mixture of the polycarbonate pellets and the additives is thoroughly shaken in order to homogeneously distribute the additives on the pellets. All amounts of the additives are based on the weight of the polycarbonate. The mixture is extruded to granules at a temperature of 365° C. The extrusion is carried out under vented conditions (300 rpm, 55 to 65 % torque, double screw). The granules are injection molded at 300° C. into test bars of 3.2 mm thickness. The optical properties of the test bars are listed in Table 1 below.
Example 2
Preparation of the Diphosphine
Bis(diphenyl 4,4'-hydroxyphenyl phosphine) terephthalic acid ester, i.e., a compound of Formula I wherein $R^2$ and $R^3$ are phenyl, $R^4$ is phenylene and A is C(O)-1,4-phenylene-C(O), is produced according to the following procedure:

5.6 g of diphenyl 4-hydroxyphenyl phosphine are brought into a flask of the type used in Example 1 and flushed with nitrogen. Then 40 mL of dichloromethane and 2 g of triethylamine are added under agitation. After complete dissolution of the diphenyl 4-hydroxyphenyl phosphine, 2.03 g of terephthaloyl chloride, dissolved in 20 mL of dichloromethane are dropped into the flask. The reaction is performed at a temperature of 25° C. After completion of the reaction, the reaction mixture is further processed as described in Example 1. A white powder of bis(diphenyl 4,4'-hydroxyphenyl phosphine) terephthalic acid ester is obtained.

The melting point Fp of the compound is 156° C., as measured by Differential Scanning Calorimetry. The structure of the compound is confirmed by IR, $^1$H—NMR and $^{31}$P—NMR. The purity of the compound is 97–98%, the yield is 69.4%, based on the amount of diphenyl hydroxyphenyl phosphine.

IR-Spectrosopy: 1736 cm$^{-1}$ (C=O); 1583 cm$^{-1}$ (C—C atomate); 1491 cm$^{-1}$ (C—C aromate); 744 cm$^{-1}$ (mono-substituted aromate); 699 cm$^{-1}$ (mono-substituted aromate.

$^{13}$C—NMR (CDCl$_3$): 128 ppm (aromate); 130–132 ppm (phenylene of the terephthaloyle-unit); 133,135 ppm (aromate); 164 ppm (C=O, ester-bond).

$^{31}$P—NMR (CDCl$_3$): −5.82 (Singulett, phosphine) (calibrated with H$_3$PO$_3$).

The weight loss of the compound is measured by the same method as in Example 1.

| Temperature (°C.) | Weight loss (%) |
|---|---|
| 302 | 4 |
| 386 | 9.7 |
| 420 | 23.4 |
| 447 | 38 |
| 590 | 67.1 |

The comparison with triphenyl phosphine shows that the compound of the present invention is much less volatile than triphenyl phospine which volatilizes completely at TGA test conditions at 300° C.

Use of the Diphosphine as a Stabilizer

Test bars are prepared in the same manner as in Example 1, except that bis(diphenyl 4,4'-hydroxyphenyl phosphine) terephthalic acid ester is used as a stabilizer. The optical properties of the produced test bars are listed in Table 1 below.

Example 3 and Comparative Examples A to D

Test bars are prepared in the same manner as in Example 1, however other types and/or amounts of heat stabilizer are used, as listed in Table 1 below. The optical properties of the produced test bars are listed in Table 1 below.

Example 4 and Comparative Example E

Test bars are produced in the same manner as in Example 3 and Comparative Examples A to D, however, 1% of an organic light diffuser is used instead of a combination of barium sulphate and titanium dioxide. The organic light diffuser is a polymer having a core of poly(butyl acrylate) and a shell of poly(methyl methacrylate). It is commercially available from Rohm and Haas under the trademark Paraloid EXL 5137.

TABLE 1

| (Comparative) Examples | Stabilizer Type/Content (ppm) | Total Light Transmittance | Light Diffusion | Yellowness index YI |
|---|---|---|---|---|
| 1 | I/500 | 58% | 48% | 11.7 |
| 2 | II/500 | 57% | 48% | 10.6 |

TABLE 1-continued

| (Comparative) Examples | Stabilizer Type/Content (ppm) | Total Light Transmittance | Light Diffusion | Yellowness index YI |
|---|---|---|---|---|
| 3 | II/1000 | 58% | 48% | 8.6 |
| A | III/1000 | 58% | 48% | 10.0 |
| B | III/2000 | 59% | 49% | 9.4 |
| C | IV/1000 | 58% | 48% | 10.9 |
| D | none | 53% | 44% | 23.5 |
| 4* | I/500 | 62% | 52% | 5.3 |
| E* | none | 64% | 53% | 7.8 |

*other organic light diffuser than in Examples 1–3 and A–D

Visual comparison between Example 3 and Comparative Examples A and B, which make use of triphenyl phosphine as a stabilizer, shows that the test bar of Example 3 has the whitest color. This finding is confirmed by the lowest Yellowness Index. In the tests made for Comparative Examples A and B triphenyl phosphine was detected at the die and at the extruder vent. In the test made for Example 3 the diphosphine could neither be detected at the die nor at the extruder vent.

Example 5 and Comparative Examples F to J

Polycarbonate pellets prepared by interfacial polycondensation of bisphenol A and phosgene and comprising 0.5% of a branching agent are used as a base resin. The polycarbonate has a melt flow rate of 3.0. The polycarbonate comprises 400 ppm of tri-(2,4-di-tert. butyl-phenyl)phosphite as an additional heat stabilizer. 1000 ppm of Cetiol (trademark) as a tackifier is homogeneously distributed on the polycarbonate pellets. Then a stabilizer of the type and concentration listed in Table 2 below is added. All amounts of the additives are based on the weight of the polycarbonate. The mixture is extruded to granules at a temperature of 298° C. The granules are injection molded at 300° C. into test bars of 3.2 mm thickness. The Yellowness Index YI of the test bars are listed in Table 2 below.

TABLE 2

| (Comparative) Examples | Stabilizer Type/Content (ppm) | Yellowness Index YI |
|---|---|---|
| F | none | 3.5 |
| G | IV/1000 | 3.3 |
| H | V/1000 | 4.2 |
| 5 | II/1000 | 3.0 |
| I | III/1000 | 3.1 |
| J | III/2000 | 3.2 |

The results of Table 2 illustrate a diphosphine of the present invention (Example 5) is a considerably better heat stabilizer than the diphosphine of Comparative Example H. In these tests the Yellowness Index of the test bar produced according to Example 6 is even lower than the Yellowness Index of the test bars produced according to Comparative Examples I and J which comprise triphenyl phosphine as a stabilizer.

Example 6

Preparation of the Diphosphine

Bis(diphenyl 4,4'-phenoxy phosphine) dimethyl silane, i.e., a compound of Formula I wherein R$^2$ and R$^3$ are phenyl, R$^4$ is phenylene and A is —(CH$_3$)Si(CH$_3$)— is produced according to the following procedure:

5.6 g of diphenyl 4-hydroxyphenyl phosphine are brought into a flask of the type used in Example 1 and flushed with nitrogen. Then 40 mL of dichloromethane and 2 g of triethyl amine are added under agitation. After complete dissolution of the diphenyl 4-hydroxyphenyl phosphine, 1.3 g of dichloro dimethyl silane, dissolved in 20 mL of dichloromethane are dropped into the flask. The reaction is performed at a temperature of 25° C.

After completion of the reaction, the reaction mixture is further processed as described in Example 1. Bis(diphenyl 4,4'-phenoxy phosphine) dimethyl silane of light yellow color is obtained. The yield of the compound is 73.4%, based on the amount of diphenyl hydroxyphenyl phosphine.

$^1$—H—NMR (CDCl$_3$, TMS): 0.41 ppm, (O—Si—CH$_3$); 6.75–6.9, 7.2–7.4 (phenylene).

$^{31}$—P (CDCl$_3$, H$_3$PO$_3$): −6.88 pppm (phosphine, singulett).

Use of the Diphosphine as a Stabilizer

Polycarbonate pellets prepared by interfacial polycondensation of bisphenol A and phosgene are used as a base resin. The polycarbonate has a melt flow rate of 3.5 and a Yellowness Index of 1.9. 1000 ppm of the Stabilizer VI of Example 6 are dispersed in 2000 ppm of Cetiol (trademark) at 70° C. The dispersion is homogeneously distributed on the polycarbonate pellets. Then 2.25% of barium sulphate (commercially available as K3 from Sachtleben), 150 ppm of titanium dioxide, 4000 ppm of Tinuvin 234 (rademark) as a UV stabilizer and 1300 ppm of Uvitex (trademark) as an optical brightener are added. All amounts of the additives are based on the weight of the polycarbonate. The mixture is extruded to granules and then injection molded at 300° C. into test bars in the same manner as in Example 1. The optical properties of the test bars are listed in Table 3 below.

Comparative Examples K to M

Test bars are prepared in the same manner as in Example 6, however only 1000 ppm of Cetiol (trademark) are used as a tackifier (instead of 2000 ppm) and other types and/or amounts of stabilizer are used, as listed in Table 3 below. The optical properties of the produced test bars are listed in Table 3 below.

TABLE 3

| (Comparative) Examples | Stabilizer Type/Content (ppm) | Total Light Transmittance | Light Diffusion | Yellowness Index YI |
|---|---|---|---|---|
| 6 | VI/1000 | 62% | 51% | 10.4 |
| K | none | 60% | 50% | 19.4 |
| L | IV/1000 | 61% | 51% | 11.5 |
| M | III/1000 | 63% | 52% | 10.6 |

What is claimed is:

1. A diphosphine of the general Formula I:

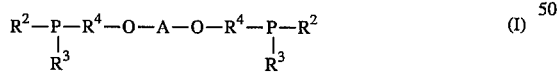

wherein:

R$^2$ and R$^3$ independently from each other represent an alkyl, cycloalkyl, aryl or aryl-alkyl group or an aryl group which is substituted at the aromatic ring with one or more radicals selected from the group consisting of halogen, alkyl and alkoxy, R$^4$ represents an alkylene, cycloalkylene, arylene or arylalkylene group or an arylene group which is substituted at the aromatic ring with one or more radicals selected from the group consisting of halogen, alkyl and alkoxy, and A is —C(O)—, —S(O)2—, —S(O)—, —C(O)-alkylene-C(O)— or —C(O)-arylene-C(O)—, the arylene group being optionally substituted at the aromatic ring with one or more radicals selected from the group consisting of halogen, alkyl, cycloalkyl, aryl, oxyalkyl, hydroxy, alkoxy and —C(O)—[O—R$^4$—P(R$^2$)(R$^3$)], and the alkylene group being optionally substituted with one or more radicals selected from the group consisting of halogen, alkyl, cycloalkyl, aryl, oxyalkyl, hydroxy, alkoxy and —C(O)—[O—R$^4$—P(R$^2$)(R$^3$)], or A is $$-\overset{|}{P}(O)[O-R^4-P(R^2)(R^3)],\quad -\overset{|}{P}(O)(R^6),\quad -\overset{|}{Si}(R^7)(R^8),$$

$$-\overset{|}{Si}(R^9)[O-R^4-P(R^2)(R^3)]\text{ or }-\overset{|}{Si}[O-R^4-P(R^2)(R^3)]_2,$$

wherein

R$^6$, R$^7$, R$^8$ and R$^9$ independently from each other represent an alkyl, cycloalkyl, aryl or aryl-alkyl group or an aryl group which is substituted at the aromatic ring with one or more radicals selected from the group consisting of halogen, alkyl, cycloalkyl, aryl, oxyalkyl, hydroxy and alkoxy.

2. The diphosphine of claim 1 wherein, in group A, the alkylene group is a C$_{1-50}$-alkylene group which is optionally substituted with one or more alkyl or alkoxy groups and the arylene group is phenylene which is optionally substituted at the aromatic ring with one or more radicals selected from the group consisting of halogen, alkyl, cycloalkyl and alkoxy.

3. The diphosphine of claim 1 wherein R$^2$ and R$^3$ represent an aryl group and R$^4$ represents an arylene group, the aryl and/or arylene groups being optionally substituted at the aromatic ring with one or more radicals selected from the group consisting of halogen, alkyl and alkoxy.

4. The diphosphine of claim 2 wherein R$^2$ and R$^3$ represent an aryl group and R$^4$ represents an arylene group, the aryl and/or arylene groups being optionally substituted at the aromatic ring with one or more radicals selected from the group consisting of halogen, alkyl and alkoxy.

5. The diphosphine of claim 1 wherein R$^2$ and R$^3$ represent a phenyl group, R$^4$ represents a phenylene group and A represents —C(O)— or —C(O)-phenylene-C(O)—.

6. A process for preparing the diphosphine of the general Formula I:

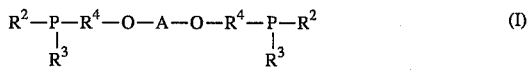

wherein:

R$^2$ and R$^3$ independently from each other represent an alkyl, cycloalkyl, aryl or aryl-alkyl group or an aryl group which is substituted at the aromatic ring with one or more radicals selected from the group consisting of halogen, alkyl and alkoxy, R$^4$ represents an alkylene, cycloalkylene, arylene or arylalkylene group or an arylene group which is substituted at the aromatic ring with one or more radicals selected from the group consisting of halogen, alkyl and alkoxy, and A is —C(O)—, —S(O)2—, —S(O)—, —C(O)-alkylene-C(O)— or —C(O)-arylene-C(O)—, the arylene group being optionally substituted at the aromatic ring with one or more radicals selected from the group consisting of halogen, alkyl, cycloalkyl, aryl, oxyalkyl, hydroxy and alkoxy, and the alkylene group being optionally substituted with one or more radicals selected from the group consisting of halogen, alkyl, cycloalkyl, aryl, oxyalkyl, hydroxy and alkoxy, or A is $$-\overset{|}{P}(O)(R^6) \quad \text{or} \quad -\overset{|}{Si}(R^7)(R^8),$$

wherein

R⁶, R⁷ and R⁸ s independently from each other represent an alkyl, cycloalkyl, aryl or aryl-alkyl group or an aryl group which is substituted at the aromatic ring with one or more radicals selected from the group consisting of halogen, alkyl, cycloalkyl, aryl, oxyalkyl, hydroxy and alkoxy, wherein a compound of Formula II:

$$R^2-\underset{R^3}{\overset{|}{P}}-R^4-OH \qquad (II)$$

wherein

R², R³ and R⁴ have the meanings as indicated in Formula I, is reacted with a compound of Formula III:

$$X-A-X \qquad (III)$$

wherein A has the meaning as indicated in Formula I and each X independently is halogen, hydroxy or alkoxy or both X together are an anhydride group, the molar ratio between the compound of Formula II and the compound of Formula III being at least 1.7:1.

7. The process of claim 6 wherein, in group A, the alkylene group is a $C_{1-50}$-alkylene group which is optionally substituted with one or more alkyl or alkoxy groups and the arylene group is phenylene which is optionally substituted at the aromatic ring with one or more radicals selected from the group consisting of halogen, alkyl, cycloalkyl and alkoxy.

8. The process of claim 6 wherein R² and R³ represent an aryl group and R⁴ represents an arylene group, the aryl and/or arylene groups being optionally substituted at the aromatic ring with one or more radicals selected from the group consisting of halogen, alkyl and alkoxy.

9. The process of claim 6 wherein R² and R³ represent a phenyl group, R⁴ represents a phenylene group and A represents —C(O)— or —C(O)-phenylene-C(O)—.

10. A polymer composition comprising a thermoplastic polymer and a thermal stabilizing quantity of a diphosphine of the general Formula I:

$$R^2-\underset{R^3}{\overset{|}{P}}-R^4-O-A-O-R^4-\underset{R^3}{\overset{|}{P}}-R^2 \qquad (I)$$

wherein:

R² and R³ independently from each other represent an alkyl, cycloalkyl, aryl or aryl-alkyl group or an aryl group which is substituted at the aromatic ring with one or more radicals selected from the group consisting of halogen, alkyl and alkoxy, R⁴ represents an alkylene, cycloalkylene, arylene or arylalkylene group or an arylene group which is substituted at the aromatic ring with one or more radicals selected from the group consisting of halogen, alkyl and alkoxy, and A is —C(O)—, —S(O)2—, —S(O)—, —C(O)-alkylene-C(O)— or —C(O)-arylene-C(O)—, the arylene group being optionally substituted at the aromatic ring with one or more radicals selected from the group consisting of halogen, alkyl, cycloalkyl, aryl, oxyalkyl, hydroxy, alkoxy and —C(O)—[O—R⁴—P(R²)(R³)], and the alkylene group being optionally substituted with one or more radicals selected from the group consisting of halogen, alkyl, cycloalkyl, aryl, oxyalkyl, hydroxy, alkoxy and —C(O)—[O—R⁴-P(R²)(R³)], or A is $$-C(O)-[O-R^4-P(R^2)(R^3)], \quad \text{or A is}$$

$$-\overset{|}{P}(O)[O-R^4-P(R^2)(R^3)], \quad -\overset{|}{P}(O)(R^6), \quad -\overset{|}{Si}(R^7)(R^8),$$

$$-\overset{|}{Si}(R^9)[O-R^4-P(R^2)(R^3)] \text{ or } -\overset{|}{Si}[O-R^4-P(R^2)(R^3)]_2,$$

wherein

R⁶, R⁷, R⁸ and R⁹ independently from each other represent an alkyl, cycloalkyl, aryl or aryl-alkyl group or an aryl group which is substituted at the aromatic ring with one or more radicals selected from the group consisting of halogen, alkyl, cycloalkyl, aryl, oxyalkyl, hydroxy and alkoxy.

11. The polymer composition of claim 10 wherein at least a portion of the thermoplastic polymer is a polycarbonate.

12. The polymer composition of claim 10 in the form of granules or pellets or in the form of a molded article.

13. The polymer composition of claim 10 comprising from 0.001 to 2.5 weight percent of one or more diphosphines of Formula I, based on the weight of the thermoplastic polymer.

14. The polymer composition of claim 11 comprising from 0.001 to 2.5 weight percent of one or more diphosphines of Formula I, based on the weight of the thermoplastic polymer.

15. The polymer composition of claim 11 comprising a diphosphine of Formula I wherein R² and R³ represent a phenyl group, R⁴ represents a phenylene group and A represents —C(O)— or —C(O)-phenylene-C(O)—.

16. A method of stabilizing a thermoplastic polymer against thermal discoloration, which method comprises contacting the thermoplastic polymer with an effective amount of the diphosphine of claim 1.

* * * * *